(12) United States Patent
Gerdes et al.

(10) Patent No.: US 6,291,166 B1
(45) Date of Patent: Sep. 18, 2001

(54) NUCLEIC ACID ARCHIVING

(75) Inventors: John C. Gerdes, Denver; Jeffrey M. Marmaro, Aurora; Christopher A. Roehl, Denver, all of CO (US)

(73) Assignee: Xtrana, Inc., Denver, CO (US)

( * ) Notice: Subject to any disclaimer, the term of this patent is extended or adjusted under 35 U.S.C. 154(b) by 0 days.

(21) Appl. No.: 09/061,757

(22) Filed: Apr. 16, 1998

Related U.S. Application Data

(60) Provisional application No. 60/041,999, filed on Apr. 16, 1997.

(51) Int. Cl.$^7$ .............................. C12Q 1/68; C12P 19/34; C07H 21/02; C07H 21/04; C12N 15/00
(52) U.S. Cl. .......................... 435/6; 435/91.2; 536/23.1; 536/24.3; 935/76; 935/77; 935/78
(58) Field of Search ..................... 435/6, 91.2; 536/23.1, 536/24.3; 935/76, 77, 78

(56) References Cited

U.S. PATENT DOCUMENTS

| | | | |
|---|---|---|---|
| 5,506,105 | * 4/1996 | Haydock | 435/6 |
| 5,578,179 | * 11/1996 | Demorest et al. | 204/451 |
| 5,629,214 | * 5/1997 | Crosby | 436/518 |
| 5,674,997 | * 10/1997 | Woodard et al. | 536/25.4 |
| 5,863,502 | * 1/1999 | Southgate et al. | 422/58 |
| 5,863,801 | * 1/1999 | Southgate et al. | 436/63 |
| 6,043,080 | * 3/2000 | Lipschutz et al. | 435/287.2 |
| 6,066,448 | * 5/2000 | Wohlstadter et al. | 435/6 |

OTHER PUBLICATIONS

Helmuth R., in PCR Protocols: A Guide to Methods and Applications. 1990. Eds. Innis et al., Academic Press, Inc., SanDiego CA. pp. 119–128.*

Davis et al. (Eds.) Basic Methods in Molecular Biology. 1986. Elsevier Science Publishing Co., Inc. New York, New York, pp. 42–78 and 130–149.*

Polsky–Cynkin et al., Clincal Chemistry 31(9) : 1438–1443 (1985).*

Hudson J., Candian Journal of Biochemistry 49 : 631–636(1971).*

Reed et al., Nucleic Acids Research 18(10) : 3093 (1990).*

Nehls et al., Trends oin Genetics 9 (10) : 336–337 (1993).*

* cited by examiner

*Primary Examiner*—Ethan Whisenant
(74) *Attorney, Agent, or Firm*—Steven C. Petersen; Sarah O'Rourke; Hogan & Hartson, LLP

(57) ABSTRACT

This invention is directed to a process for irreversibly binding nucleic acid to solid phase and corresponding processes for the utilization thereof. Nucleic acid is bound to solid phase matrixes exhibiting sufficient hydrophilicity and electropositivity to irreversibly bind the nucleic acids from a sample. These processes include nucleic acid (double or single stranded DNA and RNA) capture from high volume:low concentration specimens, buffer changes, washes, and volume reductions, and enable the interface of solid phase bound nucleic acid with enzyme, hybridization or amplification strategies. The invention, solid phase irreversibly bound nucleic acid, may be used, for example, in repeated analyses to confirm results or test additional genes in both research and commercial applications. Further, a method is described for virus extraction, purification, and solid phase amplification from large volume plasma specimens.

14 Claims, 13 Drawing Sheets

Panel A

Panel B

```
                              SEQUENCE LISTING

<160> NUMBER OF SEQ ID NOS: 10

<210> SEQ ID NO 1
<211> LENGTH: 21
<212> TYPE: DNA
<213> ORGANISM: Cryptosporidium parvum

<400> SEQUENCE: 1
gaggatagag gcatttggtt g                                                  21

<210> SEQ ID NO 2
<211> LENGTH: 20
<212> TYPE: DNA
<213> ORGANISM: Cryptosporidium parvum

<400> SEQUENCE: 2
gttttgtagg ggtcgctcat                                                    20

<210> SEQ ID NO 3
<211> LENGTH: 100
<212> TYPE: DNA
<213> ORGANISM: Cryptosporidium parvum

<400> SEQUENCE: 3
ctatatcgta atacgctctg attacgtagg gagtggtact cctaacagta ggcctctgat        60
ttgtcagtcg ataccgct gcgctcaaat ccttttagaa                               100

<210> SEQ ID NO 4
<211> LENGTH: 15
<212> TYPE: DNA
<213> ORGANISM: Mycobacterium tuberculosis

<400> SEQUENCE: 4
cgatcgagca agcca                                                         15

<210> SEQ ID NO 5
<211> LENGTH: 15
<212> TYPE: DNA
<213> ORGANISM: Mycobacterium tuberculosis

<400> SEQUENCE: 5
cgagccgctc gctga                                                         15
```

-continued

```
<210> SEQ ID NO 6
<211> LENGTH: 40
<212> TYPE: DNA
<213> ORGANISM: Artificial Sequence
<220> FEATURE:
<223> OTHER INFORMATION: to use with M. tuberculosis

<400> SEQUENCE: 6
accgcatcga atgcatgtct cgggtaaggc gtactcgacc                            40

<210> SEQ ID NO 7
<211> LENGTH: 40
<212> TYPE: DNA
<213> ORGANISM: Artificial Sequence
<220> FEATURE:
<223> OTHER INFORMATION: to use with M. tuberculosis

<400> SEQUENCE: 7
cgattccgct ccagacttct cgggtgtact gagatcccct                            40

<210> SEQ ID NO 8
<211> LENGTH: 28
<212> TYPE: DNA
<213> ORGANISM: Homo sapiens

<400> SEQUENCE: 8
ataatccacc tatcccagta ggagaaat                                         28

<210> SEQ ID NO 9
<211> LENGTH: 28
<212> TYPE: DNA
<213> ORGANISM: Homo sapiens

<400> SEQUENCE: 9
tttggtcctt gtcttatgtc cagaatgc                                         28

<210> SEQ ID NO 10
<211> LENGTH: 99
<212> TYPE: DNA
<213> ORGANISM: Homo sapiens

<400> SEQUENCE: 10
atcctatttg ttcctgaagg gtctagtagt tcctgctatg tcacttcccc ttggttctct      60
catctggcct ggtgcaatag gccctgcatg cactggatg                             99
```

NUCLEIC ACID ARCHIVING

RELATED APPLICATIONS

This application claims priority to provisional patent application Ser. No. 60/041,999, filed 16 Apr. 1997.

FIELD OF INVENTION

This invention relates to the general fields of molecular biology, biochemistry, genetics, and biological research, and specifically, relates to a method for capturing and irreversibly binding nucleic acid from any biological specimen onto a solid phase matrix such that the bound nucleic acid can be washed extensively with aqueous buffers without elution from the solid phase. Further, the solid phase bound nucleic acid can be utilized directly as an accessible substrate for enzyme reactions or hybridization primer or probe complementary base pairing and subsequent detection, either with or without amplification. Solid phase bound nucleic acid can be introduced into hybridization or amplification reactions, not just once, but multiple times. This method, thus, further relates to commercial applications interfacing nucleic acid capture with nucleic acid hybridization and/or amplification.

BACKGROUND AND PRIOR ART

The molecular structure of nucleic acids provides for specific detection by means of complementary base pairing of oligonucleotide probes or primers to sequences that are unique to specific target organisms or tissues. Since all biological organisms or specimens contain nucleic acid of specific and defined sequences, a universal strategy for nucleic acid detection has extremely broad applications in a number of diverse research and development areas as well as commercial industries. The potential for practical uses of nucleic acid detection was greatly enhanced by the description of methods to amplify or copy, with fidelity, precise sequences of nucleic acid found at low concentration to much higher copy numbers, so that they are more readily observed by detection methods.

The original amplification method is the polymerase chain reaction described by Mullis et al. (U.S. Pat. No. 4,683,195, U.S. Pat. No. 4,683,202, and U.S. Pat. No. 4,965,188, all of which are specifically incorporated herein by reference). Subsequent to the introduction of PCR, a wide array of strategies for amplification have been described. See, for example, U.S. Pat. No. 5,130,238 to Malek, nucleic acid sequence based amplification (NASBA); U.S. Pat. No. 5,354,668 to Auerbach, isothermal methodology; U.S. Pat. No. 5,427,930 to Buirkenmeyer, ligase chain reaction; and, U.S. Pat. No. 5,455,166 to Walker, strand displacement amplification (SDA); all of which are specifically incorporated herein by reference. Some of these amplification strategies, such as SDA or NASBA, require a single stranded nucleic acid target. The target is commonly rendered single stranded via a melting procedure using high temperature prior to amplification. The instant invention provides a novel mechanism for converting double stranded nucleic acid to single stranded nucleic acid without that conventional melting step.

Prior to nucleic acid amplification and detection, the target nucleic acid must be extracted and purified from the biological specimen such that inhibitors of amplification reaction enzymes are removed. Further, a nucleic acid target that is freely and consistently available for primer annealing must be provided. A wide variety of strategies for nucleic acid purification are known. These include, for example, phenol-chloroform and/or ethanol precipitation (Sambrook et al. (1989) *Molecular Cloning: A Laboratory Manual,* 2nd Ed., Cold Spring Harbor Laboratory, Cold Spring Harbor, N.Y.), high salt precipitation (Dykes (1988) *Electrophoresis* 9:359–368), proteinase K digestion (Grimberg et al. (1989) *Nucleic Acids Res* 22:8390), chelex and other boiling methods (Walsh et al. (1991) *Bio/techniques* 10:506–513) and solid phase binding and elution (Vogelstein and Gillespie (1979) *Proc. Nat. Acad. Sci. USA* 76:615–619), all of which are specifically incorporated herein by reference.

The analysis of nucleic acid targets therefore consists of three steps: nucleic acid extraction/purification from biological specimens, direct probe hybridization and/or amplification of the specific target sequence, and specific detection thereof. In currently employed conventional protocols each of these three steps is performed separately, making nucleic acid analysis labor intensive. Further, numerous manipulations, instruments and reagents are necessary to perform each step of the analysis.

Another concern with current methodologies is the significant chance of specimen cross contamination; between concurrently run specimens or from a previously amplified sample. It would be advantageous to eliminate the melt step necessary for generating single strand nucleic acid for probe hybridization or amplification primer annealing, and directly integrate the three nucleic acid analysis steps so as to simplify the analysis procedure and methodologies, as well as reduce and/or remove the risk of cross contamination. The invention discussed herein provides a method for a direct interface of the extraction and hybridization or amplification steps discussed above.

For analysis purposes, nucleic acid must frequently be extracted from extremely small specimens in which it is difficult, if not impossible, to obtain a second confirmatory specimen. Examples include analysis of crime scene evidence or fine needle biopsies for clinical testing. In such examples, the extent of the genetic testing and confirmation through replica testing is, thus, limited by the nucleic acid specimen size. Using conventional extraction protocols for these small specimens, the nucleic acid is often lost or yields are such that only a single or few amplification analyses are possible. The present invention provides a method for irreversibly binding and thus, permanently archiving, nucleic acid from specimens. That is to say, the nucleic acid is neither altered nor exhausted during analysis, and therefore, is able to be reanalyzed an unlimited number of times. This invention takes advantage of solid phase DNA binding properties known but believed by the skilled artisan to be incompatible with nucleic acid analysis. In addition, binding properties of use for RNA analysis are characterized.

Specimens that contain high levels of endogenous or background nucleic acid such as blood are extremely difficult to analyze for the presence of low level specific targets. Solid phases with high nucleic acid avidity can be utilized to irreversibly capture oligonucleotide or probe sequences. By changing buffer conditions these materials can then selectively capture target sequences even in the presence of high levels of background nucleic acid.

The requirements for binding of DNA to solid phases and subsequently being able to elute them therefrom have been described by Boom (U.S. Pat. No. 5,234,809, specifically incorporated herein by reference) and Woodard (U.S. Pat. No. 5,405,951, U.S. Pat. No. 5,438,129, U.S. Pat. No. 5,438,127, all of which are specifically incorporated herein by reference). Specifically, DNA binds to solid phases that are electropositive and hydrophilic. Solid phase materials consisting of the atoms Silicon (Si), Boron (B), or Aluminum (Al) can be rendered sufficiently hydrophilic by hydroxyl (—OH) or other groups to result in a surface that irreversibly binds DNA, while proteins or inhibitors do not bind. The binding of RNA has not been previously characterized and is revealed in the present invention. Since conventional purification methods require elution of the bound nucleic acid, these solid phase materials are described as being of no use for DNA purification. In fact, considerable effort has been expended to derive solid phase materials sufficiently electropositive and hydrophilic to adequately bind nucleic acid and yet allow for its elution therefrom. (See, for example, U.S. Pat. Nos. 5,523,392, 5,525,319 and 5,503,816 all to Woodard, and all of which are specifically incorporated herein by reference). The present invention uses solid phase matrixes to irreversibly bind nucleic acid and teaches methods for direct solid phase nucleic acid manipulation, hybridization, and/or amplification. That is, analysis is performed without elution of the nucleic acid from the solid phase.

Boom, supra, describes solid phase DNA amplification using high chaotropic salt to reversibly bind to silica. When this solid phase is placed in the amplification reaction buffer, the nucleic acid is, in fact, eluted. Therefore, the amplification actually occurs in solution, not on solid phase. Furthermore, since binding is not irreversible, the amplification can only be performed once. Del Rio et al. ((1996) *Bio/techniques* 20:970–974) describe filter entrapment of nucleic acid in a manner allowing for repeat amplification. However, they do not describe a binding mechanism that is irreversible, therefore the method is only recommended for analysis of higher nucleic acid concentrations and then, only for a limited number of analyses.

The instant invention is directed to a novel method for converting double stranded nucleic acid to single stranded nucleic acid without any melting step and provides methods for rapid DNA and RNA capture that directly interface extraction and purification with either hybridization and/or amplification. The present invention further provides a method for irreversibly binding, and thus, permanently archiving nucleic acid from specimens. The present invention uses solid phase matrixes to irreversibly bind nucleic acid and teaches true, direct solid phase manipulation and analyses including enzyme recognition, hybridization, and primer dependent amplification. True solid phase analysis provides for stringent aqueous washes, rapid automatable nucleic acid capture and purification, selective nucleic acid detection, repeat and/or expanded analysis of the bound nucleic acid, and long term storage of nucleic acid. Each of these disclosed methodologies overcomes the drawbacks of the prior art.

SUMMARY OF THE INVENTION

The instant invention is based on novel methods of using solid phases to irreversibly capture RNA, DNA or other nucleic acids as a means for: aqueous washes, buffer changes and volume reductions during procedural manipulations; rapid and immediate capture of nucleic acid as a method of automating extraction; integrating nucleic acid capture and purification with oligonucleotide or probe hybridization and/or target or signal amplification for direct analysis of nucleic acid bound to the solid phase as either single or double strands; repeat and/or expanded analysis of the bound nucleic acid following its capture onto the solid phase matrix (nucleic acid archiving); and, gravity or high flow rate solid phase chromatography as a means of either concentrating nucleic acid from large volume specimens or removing contaminant nucleic acid from aqueous buffers or solutions.

More specifically, this invention comprises the use of highly electropositive solid phase materials, generally containing Si, B, or Al atoms rendered hydrophilic by -OH or other groups, so as to result in a surface that irreversibly captures nucleic acid. Using these high affinity materials, nucleic acid is captured as double stranded nucleic acid directly from aqueous biological specimens or buffers. By adjustment of the specimen to alkaline pH or high chaotropic salt concentration, the nucleic acid is bound to the solid phase as single strand nucleic acid. Binding the nucleic acid as a single strand is necessary in order to interface with hybridization or isothermal amplification methods. The solid phase bound nucleic acid can be readily washed with aqueous buffers, thereby providing a convenient mechanism for buffer changes and volume reduction. In the preferred embodiment, this is accomplished utilizing gravity flow. The solid phase bound nucleic acid can be directly brought into contact with reaction mixtures that provide for nucleic acid hybridization, and/or signal or target amplification. The nucleic acid remains bound to the solid phase even after multiple buffer washes, hybridization, and/or amplification reactions. The ability to reanalyze the same nucleic acid specimen is a mechanism that provides a means of result confirmation and/or expanded analysis, especially useful when the specimen is available in limited quantity or cannot be replaced. Irreversibly bound nucleic acid is stable at ambient room temperature, further providing a useful method of nucleic acid storage.

The invention described herein provides a method for capturing and irreversibly binding nucleic acid, at low concentrations and at high flow rates from any biological specimen onto a solid phase matrix, such that the bound nucleic acid can be washed extensively with aqueous buffers without elution from the solid phase. This binding provides high stringency for commercial applications such as microarray hybridizations that demand low background to attain high sensitivity. This method, thus, further relates to commercial applications for automating nucleic acid extraction, concentrating low copy nucleic acid from high volume specimens, and interfacing extraction and purification with amplification or hybridization nucleic acid capture. Commercial applications include high throughput nucleic acid testing that would benefit from robotic automation, or economical screening of low prevalence targets by means of pooled specimen testing. Further, the solid phase bound nucleic acid can be directly manipulated by enzyme, hybridization, and/or amplification reactions, not just once, but multiple times. The present invention, therefore, further lends itself to applications where a biological specimen is found in limited quantity and/or might be irreplaceable and the reanalysis, either immediately or after storage of the original specimen, is beneficial. Areas where this occurs include, for example, forensics, medical and biological research, veterinary or human clinical diagnostics, dentistry, environmental, food, or water microbiology, and agricultural or other industrial applications.

Other features and advantages of the instant invention will become apparent from the following detailed description, taken in conjunction with the accompanying figures, that illustrate by way of example, the principles of the instant invention.

DETAILED DESCRIPTION OF THE PREFERRED EMBODIMENT

Figure 1:
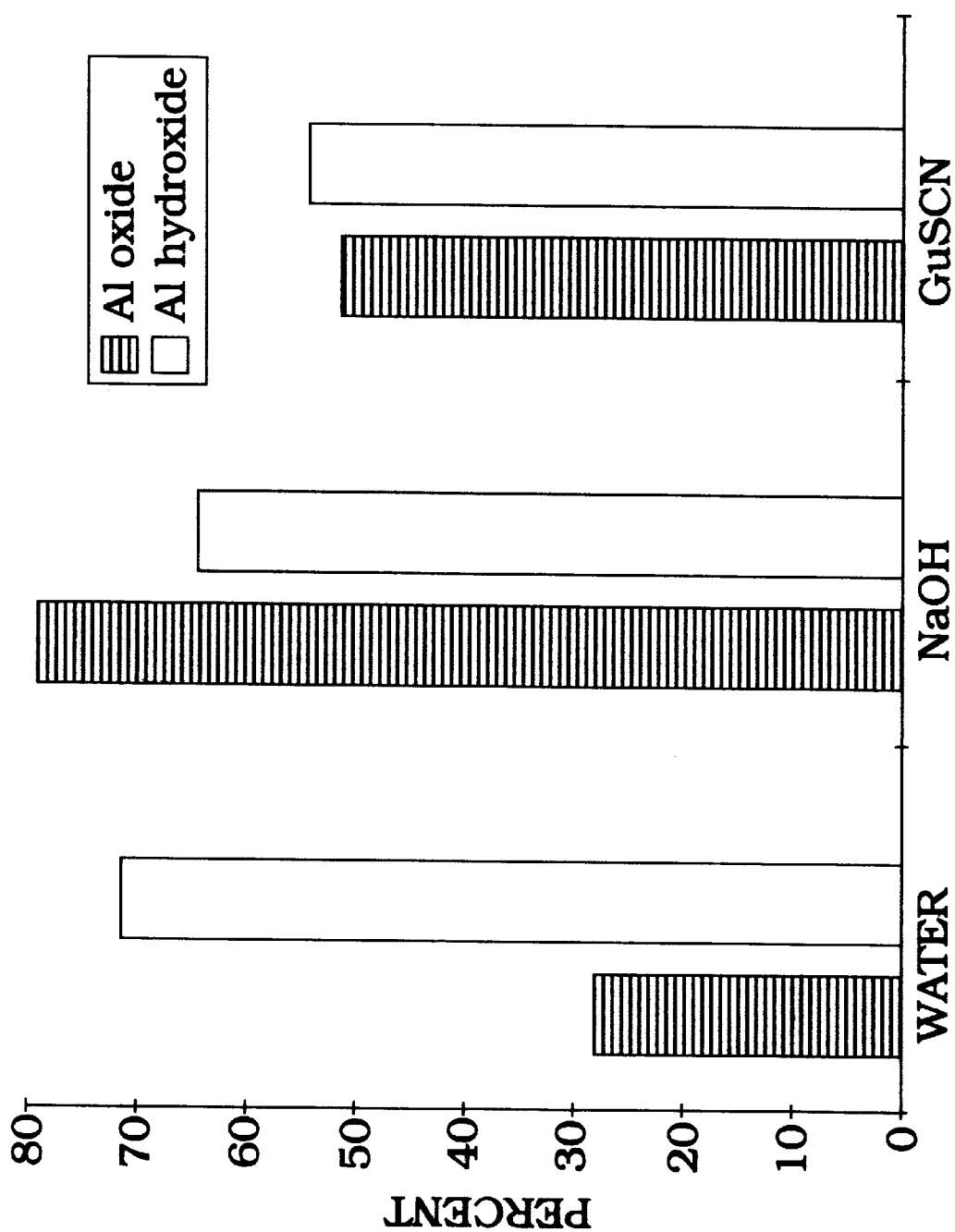
FIG. 1 is a bar graph illustrating the percentage binding of 1 nanogram of $^{32}P$ radiolabeled DNA to 198 mg of either aluminum oxide or aluminum hydroxide following one hour room temperature incubation with rotation in water, 0.1 N Sodium Hydroxide (NaOH), or 4 M guanidine thiocyanate (GuSCN) binding buffers.

It is understood that both the foregoing general description and the following detailed description are exemplary and explanatory only and are not restrictive of the invention as claimed.

The general principles and conditions for manipulations, including hybridization and amplification are well known in the art. The instant invention describes a method for capturing and irreversibly binding nucleic acid on a solid phase matrix immediately, and at high flow rates. Binding occurs for both DNA and RNA even at high volumes and low target concentrations. Irreversibly bound nucleic acid can be subjected to stringent aqueous washes, stored for later analysis, and repeatedly amplified or otherwise analyzed without elution and with no significant loss of bound nucleic acid. Repeated solid phase manipulation of any nucleic acid may be accomplished according to the present invention.

One skilled in the art recognizes that irreversible nucleic acid binding, as disclosed herein, may be performed with a broad range of biological samples. Such biological samples include, for example, biological samples derived from agriculture sources, bacterial and viral sources, and from human or other animal sources, as well as other samples such as waste or drinking water, agricultural products, processed foodstuff and air. More specifically, biological samples include, for example, blood, stool, sputum, mucus, cervical or vaginal specimens, cerebral spinal fluid, serum, urine, saliva, teardrop, biopsy samples, histological tissue samples, tissue culture product, an agricultural product, waste or drinking water, foodstuff and air. The present invention is useful for the irreversible binding of nucleic acid to a solid phase matrix from any sample containing nucleic acid, either naturally occurring or as a contaminant.

Various terms are used in this specification, for which it may be helpful to have definitions. These are provided herein, and should be borne in mind when these terms are used in the following examples and throughout the instant application.

As used herein, the term "archiving" refers to the analysis of nucleic acid irreversibly bound to a solid phase matrix via procedural manipulations followed by storage of the bound nucleic acid. Storage encompasses both the capacity for delayed analysis, and for repeated analysis of the same nucleic acid, as well as expanded analysis of multiple nucleic acid targets, either simultaneously or in series. For this, procedural manipulations include, for example, solid phase nucleic acid enzyme reactions, oligonucleotide or probe hybridization, and/or signal or target amplification reactions.

As used in this invention, a "template-dependent process" is defined as a process that involves either template-dependent recognition via a specific probe, copying procedure via signal amplification reaction, or target expansion via template dependent extension of a primer molecule. A template-dependent extension refers to nucleic acid synthesis and copy expansion of RNA or DNA target sequences, wherein the sequence of the newly synthesized strand of nucleic acid is dictated by the rules of complementary base pairing of the target nucleic acid and the primers. A template dependent process based upon complementary base pairing specifically using oligonucleotides or probes of specific sequence is known as "hybridization" detection.

A "primer" molecule refers to a nucleic acid sequence, complementary to a known portion of the target sequence/control sequence, necessary to initiate synthesis by DNA or other polymerases.

"Target nucleic acid sequence" refers to the nucleic acid molecule that is to be detected or amplified. The target molecule can be present in a purified, partially purified or unpurified state in the sample.

"Capture" refers to the binding of nucleic acid onto a solid phase matrix. Binding can be direct in appropriate buffers based on the chemical/physical properties of nucleic acid. Alternatively, capture can be target specific by irreversibly binding probes to a solid phase matrix followed by specific hybridization of a target nucleic acid.

The present invention is embodied in a method for the capture and irreversible binding of nucleic acid to a solid phase and subsequent solid phase manipulation. Regardless of the specific application of the instant invention, the methodology details are calculated according to protocols well known in the art as well as those disclosed herein. Further, the refinement of said necessary calculations is routinely made by those of ordinary skill in the art and is within the ambit of tasks routinely performed by them without undue experimentation.

This application teaches specific applications of irreversible binding of nucleic acids to solid phase materials. The known specific binding materials are characterized by atomic structure with high electropositivity that have been rendered hydrophilic. These materials have previously been considered by the skilled artisan to be of no use for nucleic acid analysis since the nucleic acid cannot be eluted. Conversely, this invention exploits this irreversible binding for specific applications.

Those skilled in the art readily recognize the present invention is broadly applicable to nucleic acid extraction, purification and detection. The following examples serve to explain and illustrate the present invention. Said examples are not to be construed as limiting of the invention in anyway. Various modifications are possible within the scope of the invention.

EXAMPLE 1

Methods and Materials

DNA binding is measured utilizing $^{32}$P radiolabeling. The 4361 base pair PBR322 plasmid, obtained from New England Biolabs is randomly prime labeled using the Prime-It II Stratagene kit. The plasmid is cut with Hind III, unlabeled nucleotides removed utilizing BioRad Biospin 6, and adjusted to a concentration of 1 nanogram per microliter (ng/$\mu$l). Higher DNA concentrations are adjusted by the addition of salmon sperm DNA. The data for radiolabeling experiments represents the mean value of 5 replica data points.

Aluminum oxide beads (74–149 $\mu$m size), obtained from Aldrich (catalog no. 34,265-3), are treated with 0.1 N NaOH for 1 hour at room temperature to produce aluminum hydroxide. DNA binding buffers consisting of water (ddH$_2$O), 0.1 N NaOH, or a 4 M guanidine thiocyanate buffer (12 g GuSCN, 277 $\mu$l Triton™ X-100, 2.2 ml 0.2 M EDTA pH 8.0, and 10 ml 0.1 M Tris-HCl pH 6.4) are used. Binding is permitted either by rotation in a closed microfuge tube or by gravity flow filtration. Large beads readily settle to the bottom of the tube without centrifugation and therefore facilitate washing. For gravity flow experiments a Spectrum SpectraMesh 43 $\mu$m filter (Spectrum, catalog no. 146530) is pressure fit into an ANSYS 4 mM chromatography column. The aluminum oxide beads are packed into this column as a liquid slurry, allowed to drain, blotted dry, washed once with 1 ml 70% ETOH and dried, prior to adding the DNA in the various binding buffers.

By way of illustration of solid phase amplification, published sequences and methods for well characterized loci are used. Further, all sequences employed in the instant experimental procedures are listed in Table I (SEQ ID NOS:1–10) shown below. Specifically, for PCR of HIV the SK38/SK39 primer set (Kellog and Kwok (1990) In *PCR Protocols: A Guide to Methods and Applications,* Innis M A et al., eds., Academic Press Inc., pp. 337–347, specifically incorporated herein by reference, SEQ ID NOS. 8–9, see Table I), the control HIV DNA plasmid obtained from Perkin Elmer (catalog no. N808-0016 ), and rtTH reverse transcriptase amplification are used. Strand displacement amplification utilizes the mycobacterium plasmid target and primer sets described by Walker et al. (1996) Clinical Chemistry 42:9–13, specifically incorporated herein by reference (SEQ ID NOS:4–7, see Table I). The human Short Tandem Repeat (STR) primer sets and protocols are the commercially available CTT And FFV multiplexes from Promega.

EXAMPLE 2

Confirmation of Irreversible Solid Phase Binding of DNA

Figure 2:
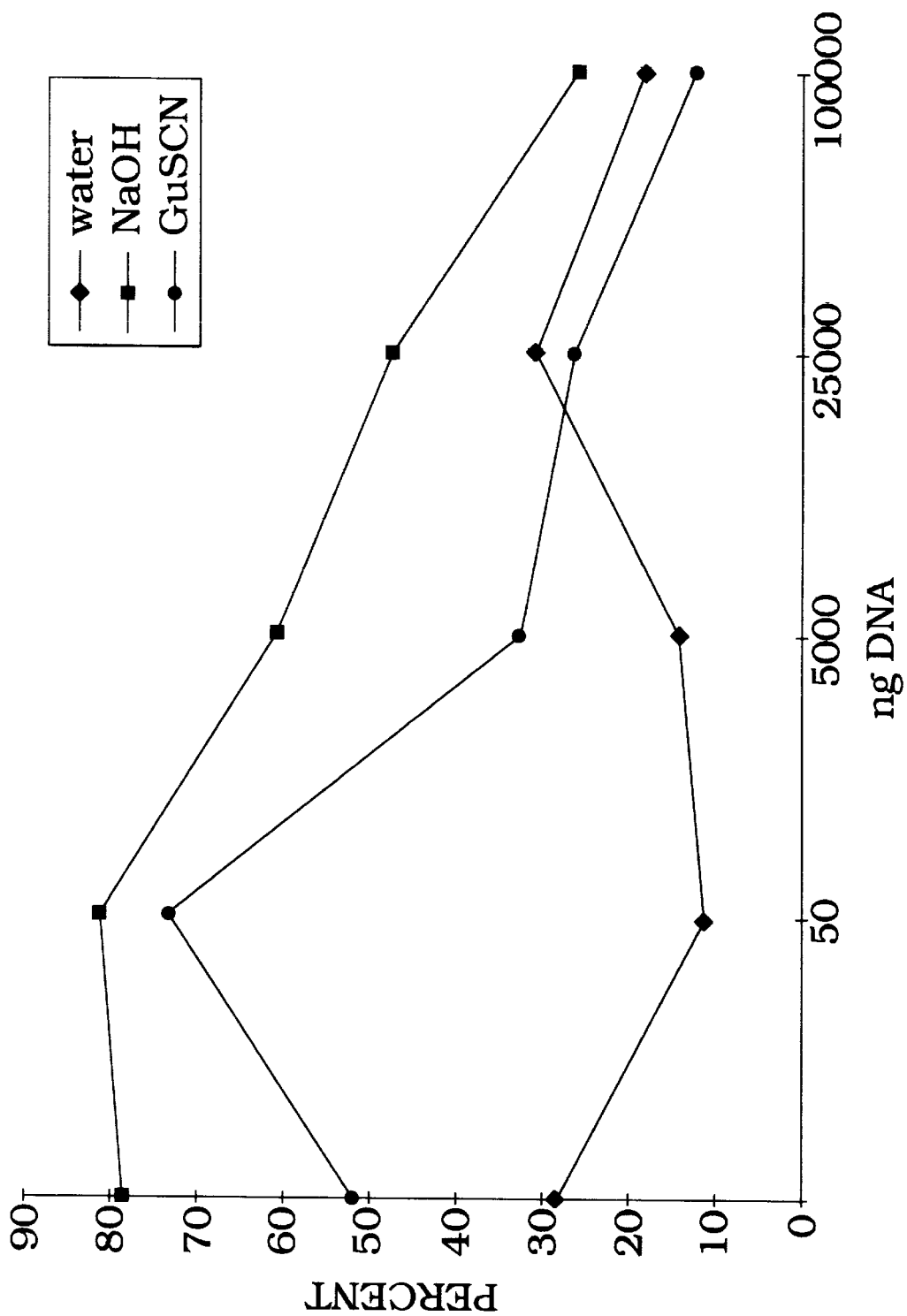
FIG. 2 is a graph illustrating the percentage of DNA bound to aluminum oxide versus the amount of DNA in nanograms (ng) following one hour room temperature incubation with rotation in water, 0.1 NaOH, or 4 M guanidine thiocyanate binding buffers.
Figure 3:
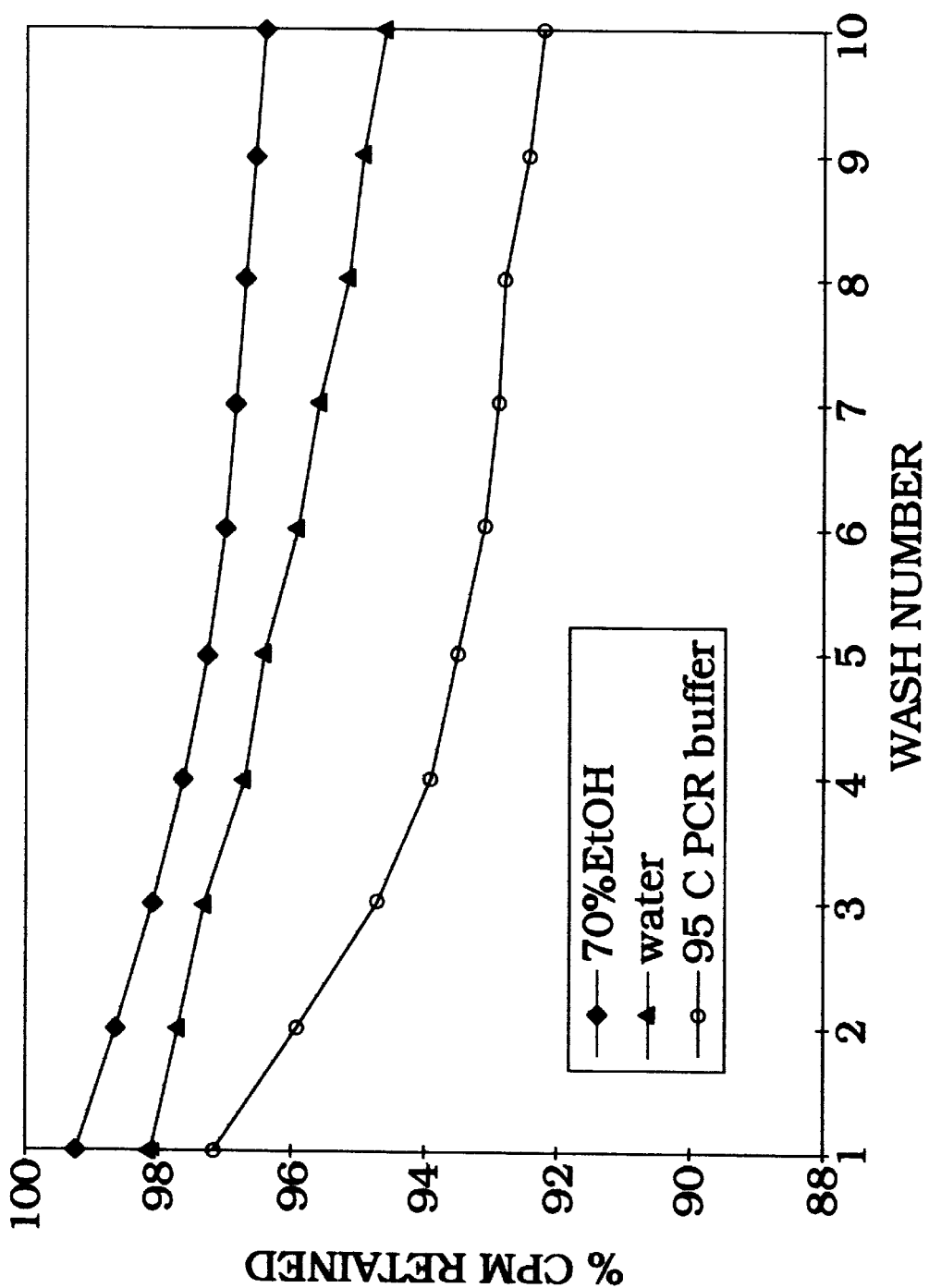
FIG. 3 is a graph illustrating the amount of radiolabeled DNA bound to aluminum oxide, shown as percent counts-per-minute (cpm) retained versus the number of times the bound DNA was washed.

Radiolabeled DNA (1 ng) is allowed to bind to either aluminum oxide or aluminum hydroxide at room temperature, with rotation, for 1 hour in water (ddH$_2$O), 0.1 N NaOH, or 4 M guanidine buffer. The DNA binds to aluminum oxide in water or guanidine thiocyanate buffer. Binding is greatly enhanced by using either NaOH as a binding buffer or aluminum hydroxide beads (FIG. 1). In order to estimate binding capacity of 198 mg aluminum oxide, 1 ng of radiolabeled DNA is added to various concentrations of salmon sperm DNA. More specifically, this procedure estimates the point at which the aluminum oxide becomes saturated so that binding of radiolabeled DNA is blocked (FIG. 2). FIG. 2, presented as the percent DNA bound versus the amount of DNA (in nanograms) bound to the aluminum oxide illustrates the effect of increasing DNA concentration on the binding efficiency of $^{32}$P radiolebeled DNA to 198 mg aluminum oxide. Water binding is saturated at 50 ng and guanidine thiocyanate buffer in the range of 50 ng to 5000 ng. Sodium hydroxide binding is not saturated until 100,000 ng. Therefore, rendering aluminum oxide hydrophilic with NaOH greatly enhances both its binding efficiency and total capacity. The irreversibility of DNA binding is shown by counting the radiolabel removed following 10 sequential washes (FIG. 3). As illustrated in FIG. 3, the DNA remains tightly bound with greater than 92% retention following 10 washes with 95° C. PCR buffer. The majority of eluted counts, (6%), occur during the first 4 washes with only a 2% total elution during the last 6 washes. Therefore, the data in FIG. 3 demonstrate that DNA bound to aluminum oxide is irreversibly bound, with greater than 90% DNA retained even after 10 washes with either 70% ethanol, water or PCR buffer at 95° C. Aluminum oxide bound DNA is, therefore, readily amenable to aqueous washes and buffer changes without centrifugation and without danger of losing the DNA. The solid phase bound nucleic acid selected from large volume samples can be washed and then resuspended at any desired volume. For example DNA can be bound to aluminum oxide from a 3 milliliter (ml) sample containing guanidine thiocyanate buffer, washed with phosphate or Tris buffer, then the beads resuspended in small volumes of amplification reaction mixtures (50 $\mu$l). These properties provide a method of simplifying the interface between DNA purification and amplification.

EXAMPLE 3

Gravity Flow Chromatograph

Figure 4:
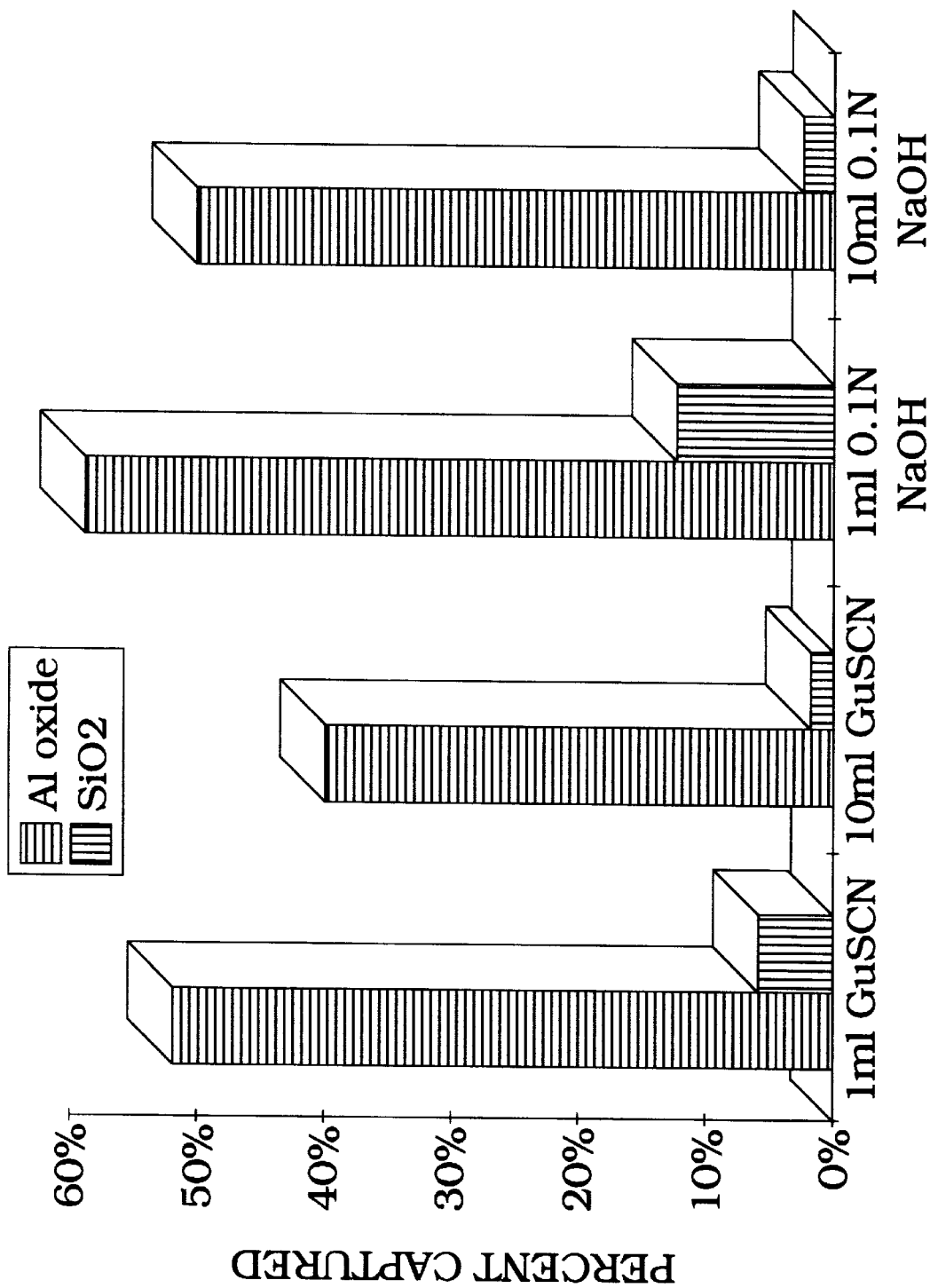
FIG. 4 is a bar graph comparing the percent DNA bound to aluminum oxide or silicon dioxide, where the DNA is diluted with either guanidine thiocyanate binding buffer or sodium hydroxide buffer.

Significant improvement in the sensitivity of DNA detection from specimens of high volume and low concentration is derived based on that capability of aluminum oxide to efficiently bind DNA at high flow rate by chromatography. Radiolabeled DNA is allowed to bind during gravity filtration of either 74–149 $\mu$m aluminum oxide beads or 150–212 $\mu$m silicon dioxide beads (Sigma, catalog no. G1145)(FIG. 4). The amount of silicon dioxide or aluminum oxide is adjusted such that they both have equal surface area available for DNA binding. DNA (50 ng) binds during gravity filtration when diluted in either 1 ml (1.5–2 minutes flow time, approximately 0.5 ml/min) or 10 ml (5–8 minute flow times, approximately 2 ml/min). FIG. 4 compares the effect of flow rate and concentration on DNA binding to silicon dioxide versus DNA binding to aluminum oxide. Aluminum oxide is much more efficient at binding DNA during gravity flow chromatography of the 1 ml volume (silicon dioxide ($SiO_2$) is 6% vs aluminum oxide ($Al_2O_3$) 52%, both in 4 M guanidine thiocyanate binding buffer). Binding efficiency for both $SiO_2$ and $Al_2O_3$ improves with 1 ml NaOH binding buffer ($SiO_2$ is 12.4% vs $Al_2O_3$ is 60%). Increasing the flow rate four fold by using the 10 ml volume and starting with the same 50 ng DNA (i.e., 10 times lower per ml concentration than the I ml specimen) drastically reduces binding efficiency of silicon dioxide to less than 2%. In contrast, aluminum oxide suffers only a 10% reduction in total count recovery. Additional experimental procedures indicate that by repeating the chromatography using a second or third pass of the high volume specimen, up to 80% efficiency of binding is obtained for aluminum oxide (now shown). Aluminum oxide is vastly superior for solid phase DNA binding compared to silicon and is capable of chromatographic capture of DNA at high flow rates and low concentrations. This property allows for use of aluminum oxide for DNA concentration from pooled or large volume specimens and provides greatly increased per milliliter sensitivity of DNA detection. The high avidity of aluminum oxide for DNA is also useful for the removal of low level DNA contaminants from water, buffers, or other reagents.

EXAMPLE 4

Solid Phase Amplification

Figure 5:
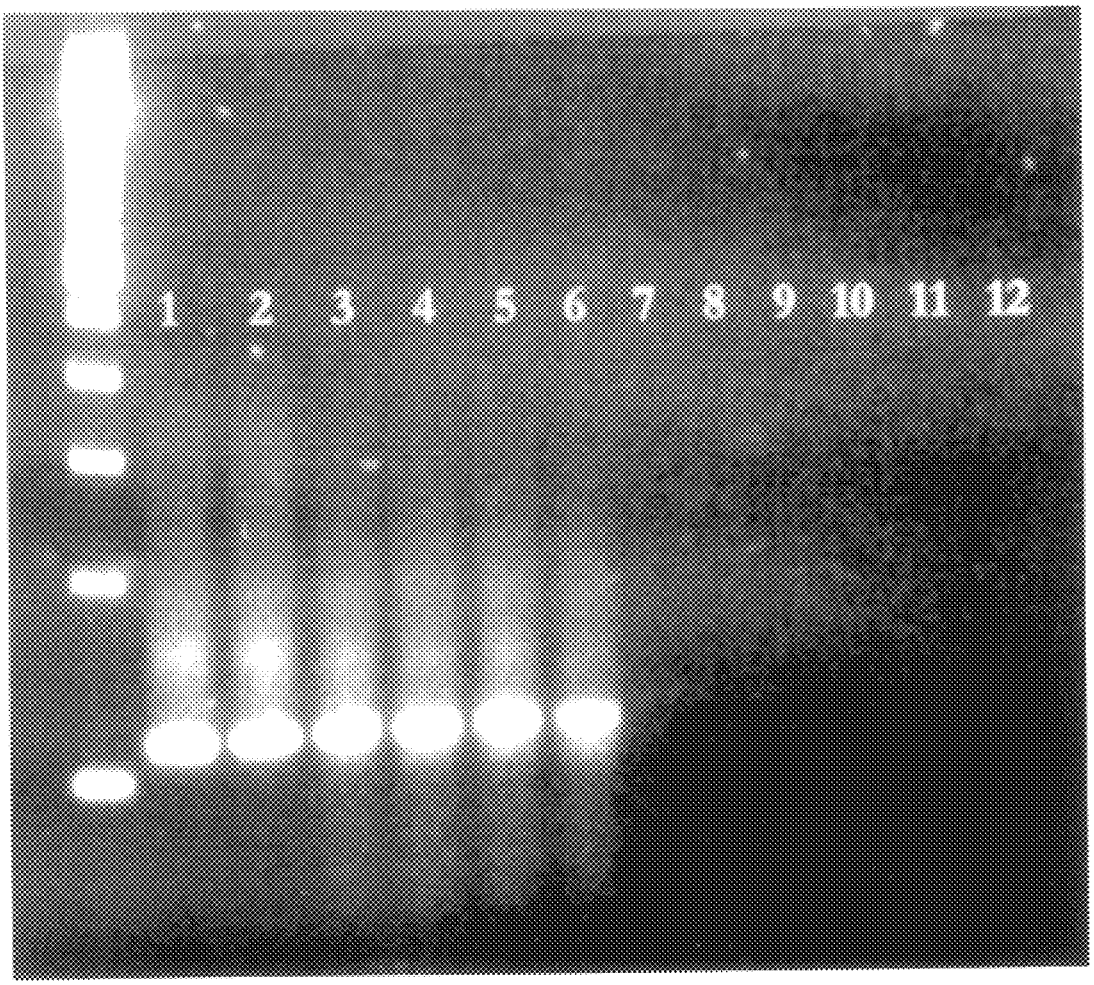
FIG. 5 panels a and b are agarose gels of $10^6$ copies of HIV DNA and 1 μl of a plasmid prep of mycobacterium DNAs bound to aluminum oxide in water, followed by direct solid phase amplification of the HIV DNA and mycobacterium in series. Panel a depicts an ethidium bromide stained agarose gel of the solid phase HIV PCR amplification product. Panel b depicts an ethidium bromide stained agarose gel of the solid phase mycobacterium DNA SDA amplification product.
Figure 5:
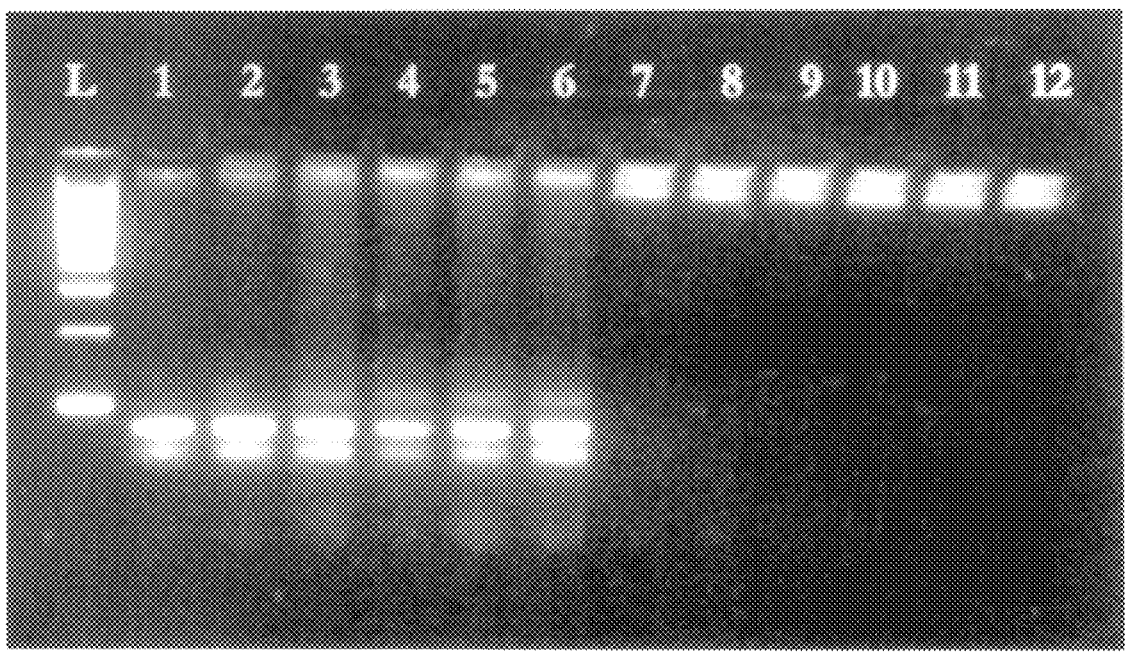

Since this nucleic acid binding is irreversible, aluminum is only useful if the bound DNA can be amplified directly on the solid phase. In order to illustrate compatibility with different amplification methods, $10^6$ copies of HIV DNA and 1 μl of a plasmid prep of mycobacterium DNAs are simultaneously bound to aluminum oxide in water. These bound DNA targets are then amplified in sequence with HIV, initially amplified using 35 cycles of polymerase chain reaction (PCR) (FIG. 5 panel a), followed by amplification of the mycobacterium target via strand displacement amplification (SDA) (FIG. 5 panel b). An ethidium bromide (EtBr) stained agarose gel of the HIV PCR, shown in FIG. 5 panel a, exhibits excellent amplification product. In FIG. 5 panel a well 1 is a molecular weight ladder, wells 2 and 3 are positive aqueous 1000 copy control amplifications, wells 4, 5, 6 and 7 are aluminum oxide phase PCR amplifications, wells 8, 9, 10 and 11 are negative aluminum oxide solid phase controls, and wells 12 and 13 are aqueous negative controls. Following the HIV PCR amplification, the aluminum oxide is washed four times with 70% ETOH, dried at 55° C. for 10 minutes, then an SDA amplification of the mycobacterium target is performed. An EtBr stained agarose gel of the SDA amplification also reveals amplification product at equivalent levels to those observed in the aqueous controls (FIG. 5 panel b). In FIG. 5 panel b wells 1 and 2 are aqueous positive controls, wells 3, 4, 5 and 6 are aluminum oxide solid phase SDA amplifications, wells 7, 8, 9 and 10 are negative aluminum oxide controls, and wells 11 and 12 are aqueous negative controls. Additional experimental procedures (now shown) show that the mycobacterium plasmid DNA is bound to aluminum oxide using either the 4 M guanidine thiocyanate buffer or 0.1 N NaOH binding buffers and SDA amplification occurs on these solid phases.

Alkaline conditions are commonly known to produce single strands. DNA is also single stranded in 4 M guanidine thiocyanate buffer (Thompson and Gillespie (1987) *Analytical Biochemistry* 163:281–291, specifically incorporated herein by reference). SDA amplification of DNA bound to aluminum oxide in NaOH or guanidine thiocyanate buffer proceeds without a melt step. These data confirm that in these binding buffers the DNA is bound as single strands and provides for a direct interface between DNA purification with aluminum oxide and isothermal amplification methods requiring a single stranded target nucleic acid.

Figure 6:
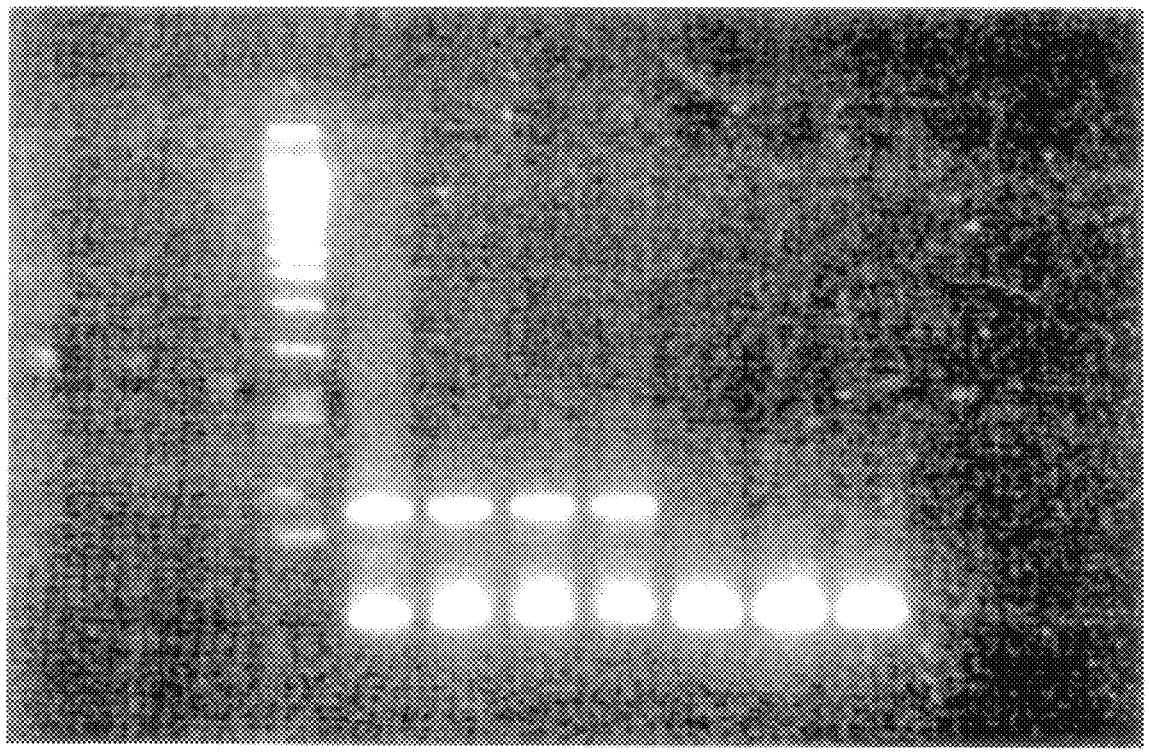
FIG. 6 is an ethidium bromide stained agarose gel of HIV RNA bound to aluminum oxide in guanidine thiocyanate buffer, followed by solid phase rtTH PCR amplification of the HIV RNA on the aluminum oxide.

To illustrate that aluminum oxide is also capable of efficient binding of RNA, the 4 M guanidine binding buffer is used with aluminum oxide purify HIV directly from an acid citrate dextrose (ACD) plasma specimen of an AIDS patient. This specimen had previously been determined by viral load quantitative PCR to have a titer of $2\times10^4$ RNA copies per milliliter. For aluminum oxide extraction, 0.5 ml of plasma is diluted to 5 ml with 4 M guanidine thiocyanate binding buffer and then gravity filtered onto 40 mg aluminum oxide. FIG. 6 shows excellent PCR product formation detected on an EtBr stained agarose gel following rtTH reverse transcriptase amplification. In FIG. 6, well 1 is a molecular weight ladder, well 2 is a 1000 copy positive aqueous HIV DNA, wells 3, 4 and 5 are rtTH reverse transcriptase amplification products following three separate guanidine thiocyanate buffer/aluminum oxide extractions, wells 6 and 7 are aluminum oxide negative controls, and well 8 is an aqueous negative control. The 4 M guanidine thiocyanate buffer protocol is capable of releasing RNA from HIV virions present in plasma, and these are captured via a high volume (5 ml) gravity filtration onto aluminum oxide in an amplifiable state. Aluminum oxide binds nucleic acids in general.

EXAMPLE 5

DNA Archiving

Figure 7:
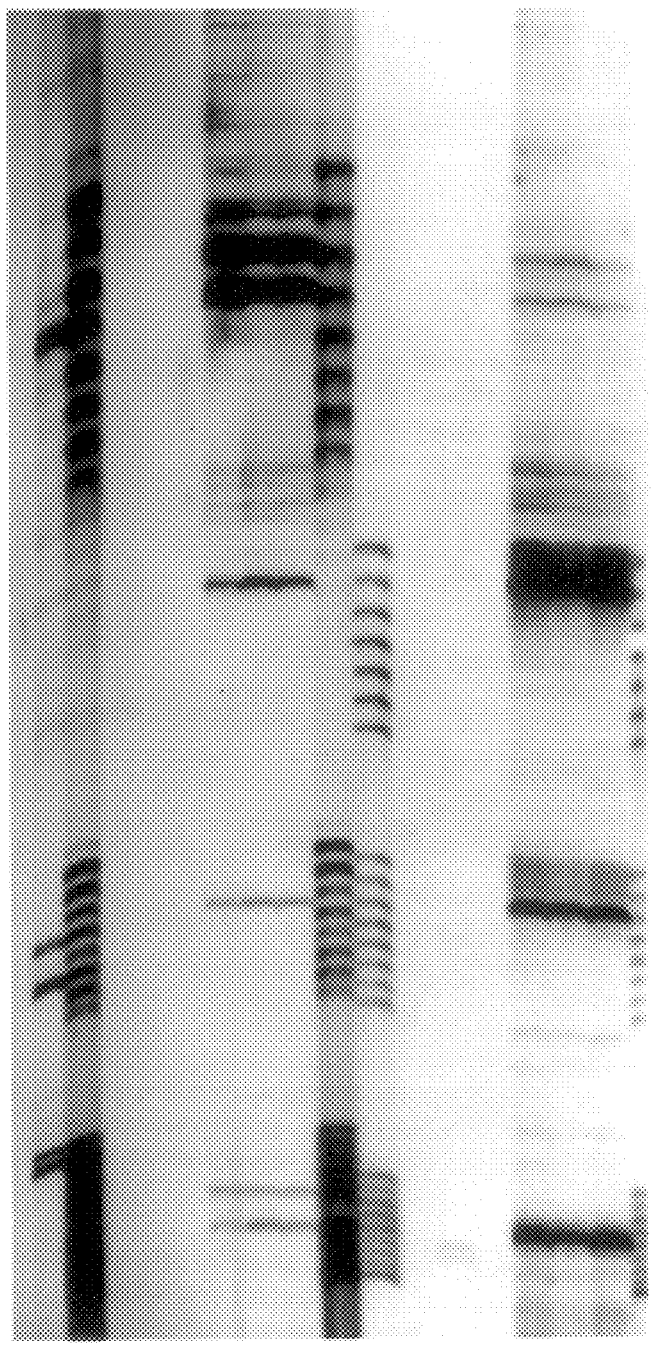
FIG. 7 is a silver stained gel after solid phase amplification of DNA on aluminum oxide with the short tandem repeat marker CTT multiplex and with the short tandem repeat marker FFV multiplex.

Combining irreversibly bound nucleic acid and direct solid phase amplification, it is possible to repeatedly analyze the same DNA sample an infinite number of times. To illustrate this point, 10 μl of ACD blood is bound to aluminum oxide in 4 M guanidine thiocyanate buffer. The bound DNA is then PCR amplified five times, 30 cycles each, using five sequential short tandem repeat (STR) amplifications using five different primer sets (Promega) in the following order: 1) F13B, 2) FESFPS, 3) VWA, 4) CTT multiplex, and 5) FFV multiplex. After the final amplification set, the DNA sample has undergone 150 PCR cycles, in toto. FIG. 7 is a silver stained gel depicting the patterns after amplification with the Promega STE CTT multiplex, which was the fourth gene set amplified, and amplifications with Promega FFV multiplex which was the fifth gene set amplified. In FIG. 7, lanes 1, 8, 9 and 16 are allelic ladders, lane 17 is human genomic aqueous positive control, lanes 2, 3, and 4 are fourth amplification (CTT multiplex) at aluminum oxide-bound DNA, lanes 5, 6 and 7 are the aluminum oxide CTT negative controls, lanes 10, 11, and 12 are the fifth amplification (FFV multiplex) of alumimun oxide bound-DNA, and lanes 13, 14 and 15 are the aluminum oxide FFV multiplex negative controls. These data confirm DNA archiving or repeated solid phase aluminum oxide amplification of the same bound DNA, following 4 M guanidine thiocyanate buffer protocol and then amplification by PCR using five sequential short tandem repeat (STM) amplifications (150 total PCR cycles). The results, shown in the silver stained gel of FIG. 7, demonstrate that amplification occurs for all 5 PCRS, thus confirming DNA archiving or repeated solid phase aluminum amplification of the bound DNA.

In summary, DNA is archived onto aluminum oxide so that it is available for additional amplification analysis. This includes repeat analysis of the same gene, serial amplification of different genes, for example, to detect different infectious agents, or expanded analysis, for example, higher discriminatory power for human identity analysis.

EXAMPLE 6

Buffers That Either Promote or Block Irreversible Binding of Nucleic Acid to Aluminum Oxide Radiolabeled DNA (50 ng) is added to 500 µl aqueous solutions of the various substances listed in Table II, below, in the presence of 198 mg aluminum oxide. In order to more accurately measure binding exclusively of radiolabeled DNA, free unincorporated nucleotides that remain following the Biospin 6 purification are determined via trichloroacetic acid (TCA) precipitation. As shown in Table II, using this corrected procedure, DNA binds to aluminum oxide at 100% efficiency in either 4 M guanidine thiocyanate buffer or sodium hydroxide. Certain other substances and/or conditions totally block the binding of DNA. In Table II, for example, these include 10% bovine serum albumin, or $K_2HPO_4$. Since both binding and blocking conditions have been defined, it is therefore possible to conveniently and specifically bind specific oligonucleotides or probes irreversibly, then change to blocking buffer conditions to allow for target specific capture by hybridization. That is, phosphate or other buffers that completely prohibit binding of nucleic acid to aluminum oxide provide the basis of hybridization buffers with low background signal to irreversibly bound nucleic acid; hybridized target is removed and the solid phase bound capture probe reused multiple times. It is well know that RNA is destroyed in 0.1 N NaOH. Therefore, by using this binding buffer DNA is exclusively captured. Efficient cell disruption and rapid nucleic acid binding with both guanidine thiocyanate buffer and sodium hydroxide buffers is effective for blood, buccal swabs, urine, and HIV virions spiked into plasma or serum. However, for certain infectious organisms, such as Cryptosporidium parvum, it is necessary to heat the specimen to 95° C. and include protein reducing agents such as dithiothreatol (DTT) in order to efficiently disrupt the cell (SEQ ID NOS:1–3, see Table I, above).

EXAMPLE 7

Figure 8:
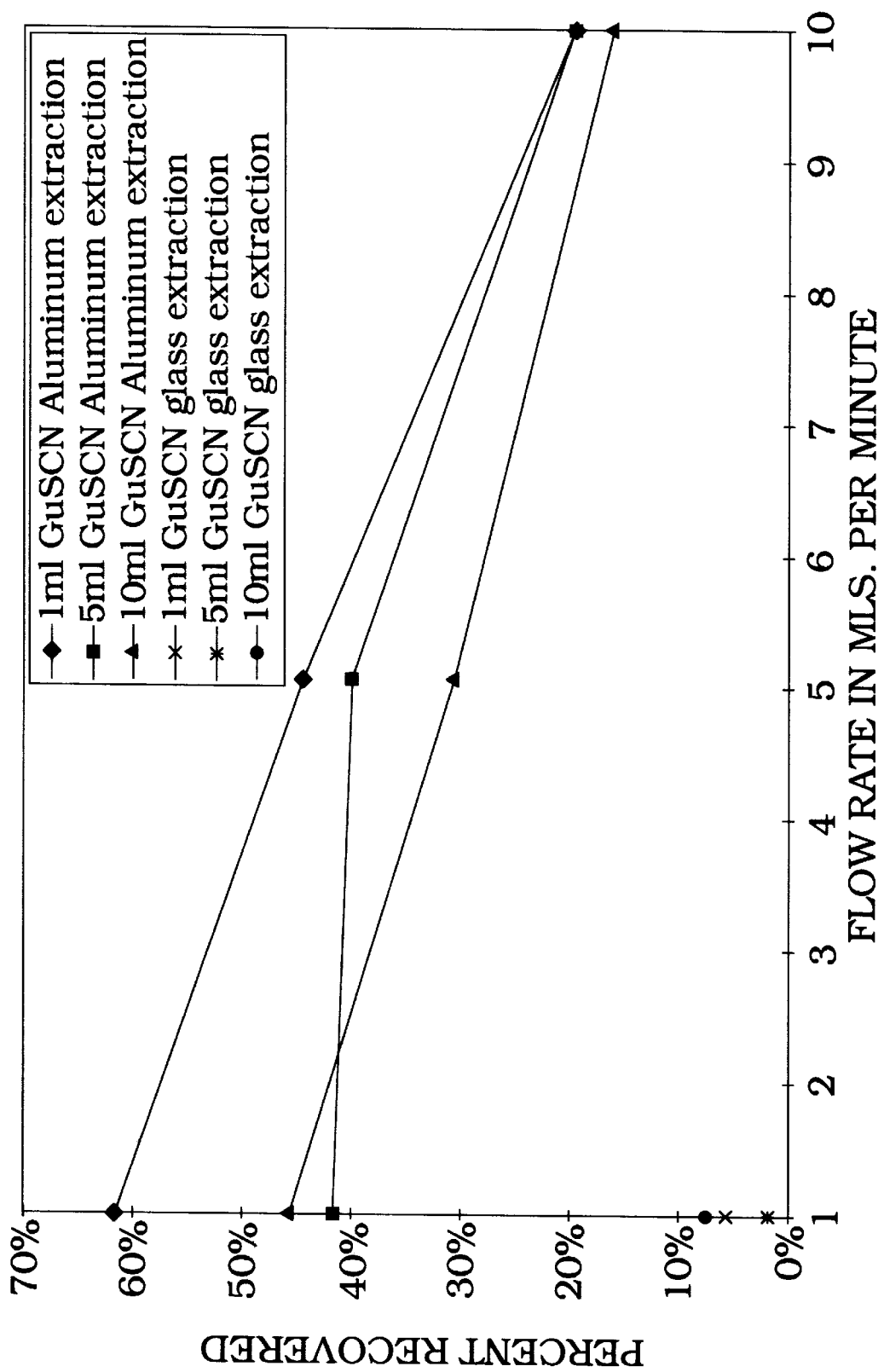
FIG. 8 depicts percent radiolabeled DNA bound to either aluminum oxide or silica dioxide for various starting volumes and at different flow rates.
Figure 9:
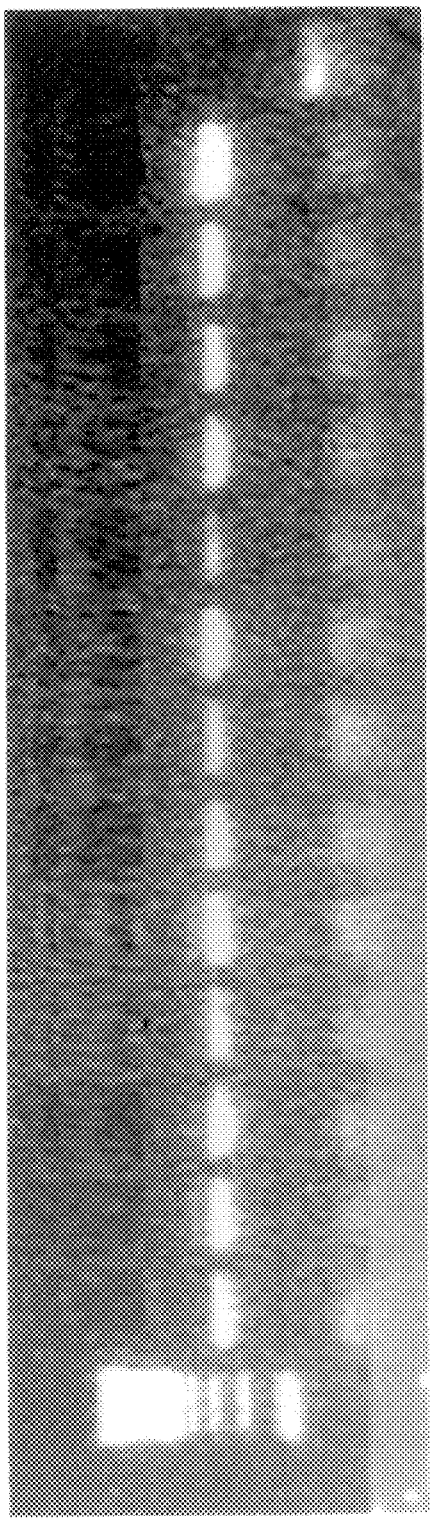
FIG. 9 depicts solid phase PCR amplification as confirmed by EtBr agarose gel using HLA DRbcta primers following irreversible capture for different capture times after addition of 50 μl ACD anticoagulated blood in the presence of 0.1 N NaOH and aluminum oxide.
Figure 10:
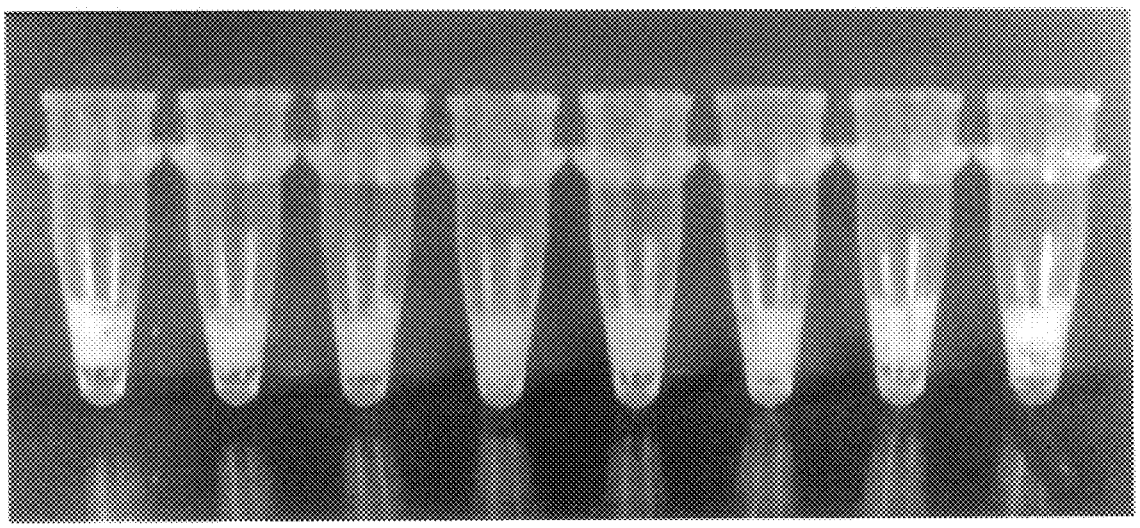
FIG. 10 shows PCR amplification tubes incorporating solid phase binding material for automated nucleic acid extraction.

Immediate Binding at High Flow Rate and Incorporation of Aluminum Oxide into PCR Tubes The capability of aluminum oxide to bind DNA at high flow rates is measured using the same total cpm of radiolabeled DNA suspended in 1 ml, 5 ml, or 10 ml of 4 M guanidine thiocyanate buffer and passing these by either aluminum oxide or silicon dioxide at measured flow rates. The results, shown in FIG. 8, confirm that aluminum oxide is vastly superior to silicon dioxide. Aluminum oxide efficiently binds nucleic acid at flow concentration, high volume (10 ml) specimens to the 1 ml specimen with 10-fold higher per ml concentration and ten fold smaller volume. DNA binding is immediate, as illustrated by the experimental results depicted in FIG. 9. Here, 50 µl of ACD anticoagulated blood is added to aluminum oxide in 0.1 N NaOH binding buffer and the HLA DR beta gene PCR amplified from the solid phase bound DNA either immediately or after permitting various incubation times for the DNA to bind. In FIG. 9, binding as indicated by the efficiency of amplification is identical for the immediate time point (lanes 1–4) the 1-minute time points (lanes 5–8) or the 2-minute time point (lane 14). Lane 13 is the aqueous negative control. These experimental results are the basis of an extremely convenient and rapid protocol for automatable nucleic acid extraction that is directly interfaced with PCR amplification. For this, aluminum oxide is adhered, via a silicon or any other adhesive shown not to inhibit PCR, into PCR tubes as shown in FIG. 10. Alternatively, it may be incorporated into a 96 PCR tube plate for higher throughput. Either of these alternatives provides for simple nucleic acid extraction by a protocol consisting of the following steps: 1) adding binding buffer to the aluminum oxide PCR tube, 2) adding specimen to each tube, mixing and then aspirating liquid to waste, 3) washing by repeat pipetting wash buffer (three times), then aspirating wash buffer to waste, 4) adding PCR amplification master mix, and 5) amplifying in a thermal cycler. The pipetting steps of this protocol are easily automated for high throughput using a robotic system.

EXAMPLE 8

Confirmation of Binding of Pure RNA to Aluminum Oxide

Figure 11:
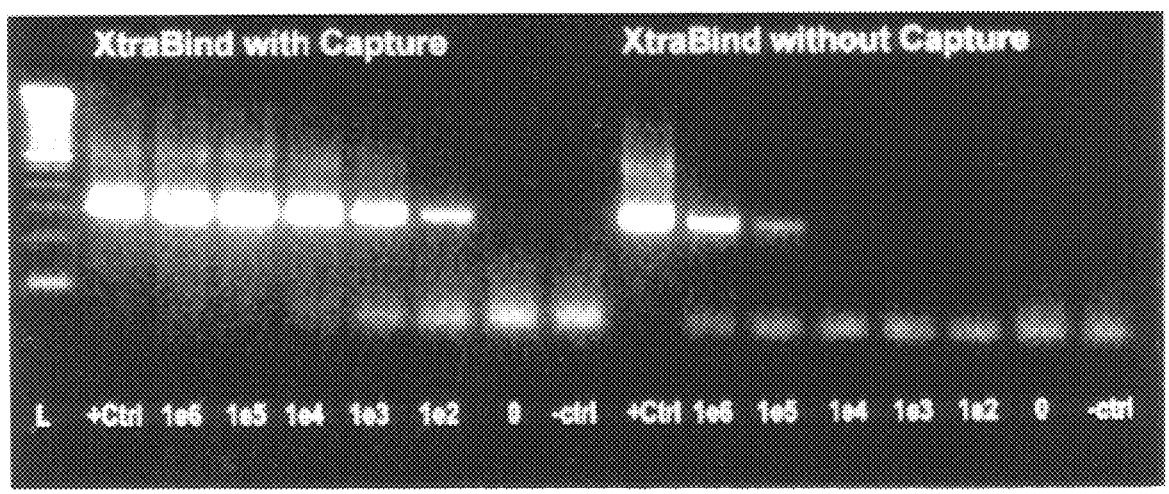
FIG. 11 is an agarose gel after solid phase PCR amplification of a pure RNA target (pAW $10^9$) after either direct binding of the RNA target onto aluminum oxide or after hybridization of the pure RNA target to an oligonucleotides capture probe that is irreversibly bound to aluminum oxide.

Example 4 suggested that RNA irreversibly binds and is amplifiable on aluminum oxide based upon the detection of HIV from a patient plasma specimen. It is possible that this result is due to contaminating proviral DNA in the serum. RNA binding using a pure RNA target confirms irreversible binding and solid phase amplification. FIG. 11 depicts the results of amplification of a pAW109 pure RNA target bound in 4 M guanidine thiocyanate buffer and rtPCR amplified on the aluminum oxide solid phase. Binding and amplification of IL-2 mRNA and Cryptosporidium parvum dsRNA on aluminum oxide (not shown) were demonstrated in a similar manner.

EXAMPLE 9

Irreversibly Bound Nucleic Acid Utilization for Specific Target Capture by Hybridization Limit of detection experiments determine that detection following PCR amplification of aluminum oxide bound DNA requires 1000 copies, and bound RNA requires $10^3$ copies (FIG. 11). Sensitivity of detection is significantly improved to less that 100 copies for either RNA or DNA using solid phase probe capture followed by hybridization. High copy capture oligonucleotide of 20–100 base pair length complementary to a sequence adjacent to the desired amplification target is irreversibly bound to aluminum oxide in 0.1 N NaOH buffer. After washing, this capture bead is used to hybridize to the target, even in specimens that contain high background levels of nucleic acid. For this procedure, the specimen is disrupted with 4 M guanidine thiocyanate buffer, diluted three fold in the presence of the solid phase matrix containing the capture probe. Hybridization is permitted to occur, and following a wash step the capture bead containing the hybridized target is directly PCR amplified. As shown in FIG. 11, this results in limits of detection of from 10–100 copies of the target.

EXAMPLE 10

Capture of Low Copy Targets in High Volume or Pooled Specimens

Figure 12:
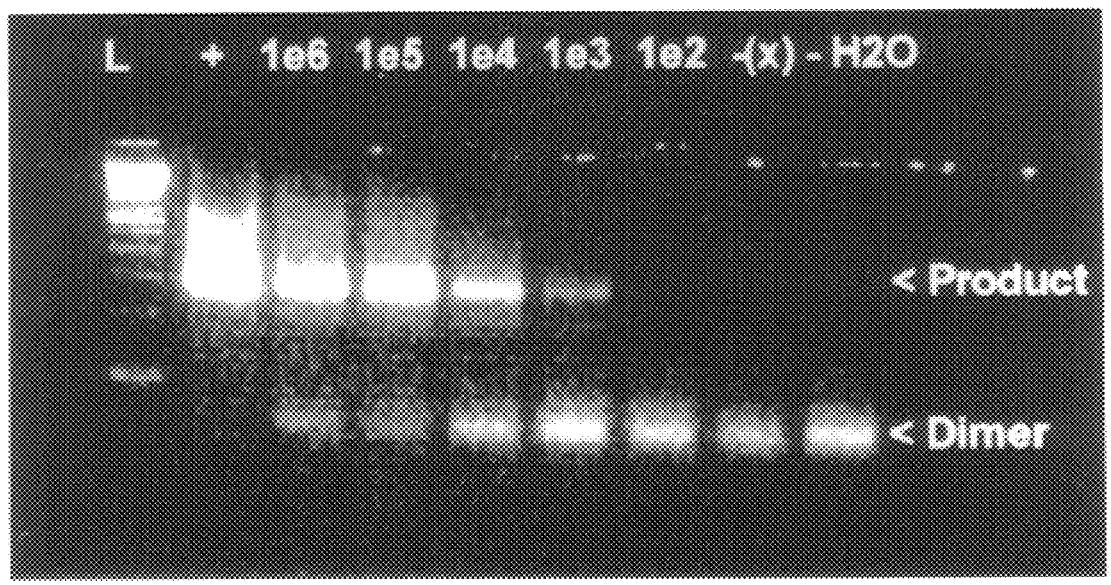
FIG. 12 shows low copy detection of 1000 copies of HIV after dilution with 5.5 mls plasma and hybridization to an oligonucleotide capture probe that is irreversibly bound to aluminum oxide beads

Hybridization capture onto solid phase probe is efficient for the specific selection of target sequences even at high initial specimen volumes. As shown in FIG. 12, 1000 copies of HIV from an AIDS patient plasma specimen is detectable with the hybridization solid phase capture procedures described above; detectable even when diluted to an initial volume of 5.5 mls with plasma. The plasma is added directly to dry guanidine thiocyanate powder for the extraction in order to minimize dilution. With this adjustment the final volume for hybridization to the capture bead is 30 mls. Additionally, positive HIV plasma at 100 µl volume is pooled with an additional 24 negative 100 µl plasma specimen, and still detected. Pooling experiments such as this confirm a detection sensitivity of 48 HIV virion copies per milliliter. Additional procedures demonstrated the detection of 100 copies of Cryptosporidium parvum pooled in 30 mls of water (not shown). The hybridization capture bead protocol, therefore, can be used to screen pooled specimens at a sensitivity almost equivalent to that for an individual specimen, carrying tremendous commercial potential since it will allow highly sensitive pooled specimen testing and providing significant reduction of cost.

EXAMPLE 11

Storage of Nucleic Acid Irreversibly Bound to Aluminum Oxide

The nucleic acid from 50 µl of ACD blood is bound onto aluminum oxide using either the 4 M guanidine thiocyanate buffer or 0.1 N NaOH buffer. The bound nucleic acid is then stored either dry, in 70 % EtOH, or in Tris EDTA buffer at room temperature, 4° C., or −20 ° C. Nucleic acid is generally stable for all of these conditions for three months, and potentially much longer utilizing the instant invention—perhaps indefinitely.

The present invention is directed to the binding of RNA to aluminum oxide and various uses for solid phase bound DNA and/or RNA. This includes methods for using aluminum oxide or other material that irreversibly binds nucleic acid for solid phase capture and directly interfaces with various manipulations; said methods using aqueous buffers, as well as for both single and in series multiplex amplification or hybridization based reactions. Further, nucleic acid capture is useful for the purpose of either removing contaminant nucleic acid, or concentrating low copy nucleic acid for the purpose of detection in either high volume or pooled specimen analysis. Aluminum oxide shows sufficient avidity for nucleic acid to bind it even at low concentrations and at high flow rates, for example, 5 ml/min. The instant invention is, thus, useful for large volume, gravity-based or high flow rate capture as well as the capture of nucleic acid in a manner compatible with extensive aqueous washes yielding extremely clean nucleic acid, free from inhibitors that may interfere with amplification reactions.

The hybridization reactions disclosed herein include direct hybridization of a target nucleic acid to an oligonucleotide probe captured on a solid phase matrix, wherein the matrix may be in the form of beads and planar surfaces such as blots or microarray chips. Hybridization may also include the specific capture of a specific sequence by irreversibly binding capture probes, for example, oligonucleotide, cDNA, cloned plasmid, transcribed or synthesized RNA, or PNA to select the complementary sequence from a complex specimen having a high background level of non-specific nucleic acid. The capture bead methodology is useful for specific sequence capture such as by utilizing poly-T oligonucleotides bound to aluminum oxide to purify poly A messenger RNA. By using the appropriate capture oligonucleotide any specific nucleic acid target can be selectively removed and concentrated from a variety of specimen types.

Also consistent with the current invention is enzyme recognition, specific manipulation or amplification reactions from nucleic acid irreversibly bound to a solid phase. This includes both target amplification reactions such as PCR, SDA, NASBA, IsoCR, or CRCA, as well as signal amplification reactions such as Q beta replicase or branched chain DNA. The incorporation of aluminum oxide as a binding substance adhered to the reaction surface area of standard PCR tubes and a protocol for rapid nucleic acid extraction that directly and conveniently interfaces with PCR thermal cycling reactions using the same tube is taught herein as well. The tubes or vessels provide a platform for automation using high throughput robotics.

Buffer systems that enable the utilization of aluminum oxide for alternative nucleic acid applications are all discussed. They include, for example, guanidine thiocyanate-based buffer including a specific reducing agent that disrupts extremely hardy specimens, such as Cryptosporidium. In this buffer, both DNA and RNA efficiently bind to aluminum oxide at close to 100% efficiency. Another buffer system is directed to alkaline buffers such as NaOH that provide a rapid and economical DNA binding buffer. In this buffer, RNA is destroyed so that this provides a means of selectively binding only DNA. Yet another system includes buffers that completely prohibit binding of nucleic acid to aluminum oxide, for example, phosphate buffer. This buffer system provides the basis of hybridization buffers with low background signal to noise for sensitive and efficient microarray, bead and blot hybridization.

The irreversible binding characteristics of, for example, aluminum oxide, provide for repeated analysis of either the same or different genes in series. This includes the analysis of both DNA and RNA simultaneously, or DNA and RNA independently but in series. By binding multiple probes, the hybridization capture can also be multiplexed for specific targets. Thus, the instant invention is useful for repeat or in series analysis of any nucleic acid by either hybridization or amplification reactions. Once irreversibly bound, nucleic acid is stable and can be stored for prolonged periods at room temperature.

While the above description contains many specificities, these specificities should not be construed as limitations on the scope of the invention, but rather exemplification of the preferred embodiment thereof. That is to say, the foregoing description of the invention is exemplary for purposes of illustration and explanation. Without departing from the spirit and scope of this invention, one skilled in the art can make various changes and modifications to the invention to adapt it to various usages and conditions. As such, these changes and modifications are properly, equitably, and intended to be within the full range of equivalence of the following claims. Thus, the scope of the invention should be determined by the appended claims and their legal equivalents, rather than by the examples provided herein.

TABLE II

Binding of Radiolabeled DNA to Aluminum Oxide

| Binding Buffer | Percent Bound | Percent Unbound |
| --- | --- | --- |
| ddH$_2$O | 20 | 80 |
| 0.1 N NaOH | 110 | 0 |
| 4M GuSCN | 104 | 0 |
| 10% BSA | 5 | 95 |
| 1M K$_2$HPO$_4$ | 4 | 96 |
| 10% Triton ™ X-100 | 64 | 36 |
| 10% Tween ™ 20 | 106 | 0 |
| 10% SDS | 12 | 88 |
| 5X SSC | 60 | 40 |

TABLE I

| ID | SEQUENCE | SEQ ID NO: |
|---|---|---|
| CPSR805F | GAGGATAGAGGCATTTGGTTG | SEQ ID NO: 1 |
| CPSR948R | GTTTTGTAGGGGTCGCTCAT | SEQ ID NO: 2 |
| CPSR100cap | CTATATCGTAATACGCTCTGATTACGTAGGGAGTGG TACTCCTAACAGTAGGCCTCTGATTTGTCAGTCGACA TACCGCTGCGCTCAAATCCTTTTAGAA | SEQ ID NO: 3 |
| B1 | CGATCGAGCAAGCCA | SEQ ID NO: 4 |
| B2 | CGAGCCGCTCGCTGA | SEQ ID NO: 5 |
| S1 | ACCGCATCGAATGCATGTCTCGGGTAAQGCGTACTC GACC | SEQ ID NO: 6 |
| S2 | CGATTCCGCTCCAGACTTCTCGGGTGTACTGAGATCC CCT | SEQ ID NO: 7 |
| SK38 | ATAATCCACCTATCCCAGTAGGAGAAAT | SEQ ID NO: 8 |
| SK39 | TTTGGTCCTTGTCTTATGTCCAGAATGC | SEQ ID NO: 9 |
| HIV cap | ATCCTATTTGTTCCTGAAGGGTACTAGTAGTTCCTGC TATGTCACTTCCCCTTGGTTCTCTCATCTGGCCTGGT GCAATAGGCCCTGCATGCACTGGATG | SEQ ID NO: 10 |

We claim:

1. A method for archiving nucleic acid, comprising:

a) irreversibly binding single- or multiple-stranded nucleic acid contained in an aqueous specimen to a solid phase matrix, wherein said matrix is defined by specific binding materials characterized by electropositive material rendered hydrophilic;

b) manipulating said solid phase bound nucleic acid; and c) storing said bound nucleic acid on said solid phase matrix.

2. The method as defined in claim 1 further comprising performing large volume gravity-based or high flow rate solid phase chromatography on said bound nucleic acid prior to storage.

3. The method as defined in claim 1 wherein said solid phase matrix is selected from the group consisting of beads and planar surfaces.

4. The method as defined in claim 3 wherein said planar surface is selected from the group consisting of blots and microarrays.

5. The method as defined in claim 1 wherein said highly electropositive material is selected from the group consisting of Silicon (Si), Boron (B) and Aluminum (Al).

6. The method as defined claim 1 wherein said specimen consists essentially of nucleic acid and buffer.

7. The method as defined in claim 6 wherein said buffer comprises a guanidine thiocyanate based buffer.

8. The method as defined in claim 6 wherein said buffer comprises an alkaline buffer.

9. The method as defined in claim 8 wherein said alkaline buffer is Sodium Hydroxide.

10. The method as defined in claim 1 wherein said manipulation methodology is selected from the group consisting of enzyme reactions, hybridization, signal amplification and target amplification.

11. The method as defined in claim 10 wherein said amplification methodology is selected from the group consisting of PCR, SDA, NASBA, IsoCR, CRCA, Q beta replicase and branched chain DNA.

12. The method as defined in claim 1 wherein said nucleic acid is naturally occurring.

13. The method as defined in claim 1 wherein said nucleic acid is non-naturally occurring.

14. The method as defined in claim 1 wherein said solid phase matrix is integrally combined with a standard polymerase chain reaction tube.

* * * * *

UNITED STATES PATENT AND TRADEMARK OFFICE
CERTIFICATE OF CORRECTION

PATENT NO.    : 6,291,166 B1  
DATED         : September 18, 2001  
INVENTOR(S)   : John C. Gerdes et al.

It is certified that error appears in the above-identified patent and that said Letters Patent is hereby corrected as shown below:

Column 1,  
Line 2, please insert the following paragraph:
-- CONTRACTUAL ORIGIN OF THE INVENTION
This invention was made with United States Government support under cooperative agreement number 70NANB5H1109 awarded by the National Institute of Standards and Technology (NIST). The United States Government has certain rights in the invention. --

Signed and Sealed this

Twentieth Day of April, 2004

JON W. DUDAS  
*Acting Director of the United States Patent and Trademark Office*